(12) United States Patent
Acosta et al.

(10) Patent No.: US 6,956,649 B2
(45) Date of Patent: Oct. 18, 2005

(54) SPECTROSCOPIC SYSTEM AND METHOD USING A CERAMIC OPTICAL REFERENCE

(75) Inventors: George M. Acosta, Phoenix, AZ (US); Kevin H. Hazen, Gilbert, AZ (US); N. Alan Abul-Haj, Mesa, AZ (US); Stephen L. Monfre, Gilbert, AZ (US); Thomas B. Blank, Chandler, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 92 days.

(21) Appl. No.: 10/723,353

(22) Filed: Nov. 25, 2003

(65) Prior Publication Data

US 2004/0169857 A1 Sep. 2, 2004

Related U.S. Application Data

(60) Provisional application No. 60/429,777, filed on Nov. 26, 2002.

(51) Int. Cl.[7] .................................................. G01J 3/28
(52) U.S. Cl. ..................................... 356/328; 356/243.1
(58) Field of Search ........................... 356/243.1, 243.4, 356/326, 328

(56) References Cited

U.S. PATENT DOCUMENTS

| | | | | | |
|---|---|---|---|---|---|
| 4,047,032 A | * | 9/1977 | Judge et al. | ............. | 356/243.4 |
| 4,647,198 A | * | 3/1987 | Sommer | ................... | 356/243.1 |
| 5,251,006 A | * | 10/1993 | Honigs et al. | ........... | 356/243.1 |
| 5,263,042 A | * | 11/1993 | Kojima et al. | ................ | 372/72 |
| 5,612,782 A | * | 3/1997 | Keranen et al. | ......... | 356/243.8 |
| 6,236,047 B1 | * | 5/2001 | Malin et al. | ............. | 250/341.8 |
| 6,497,946 B1 | * | 12/2002 | Kretman et al. | ............ | 359/515 |
| 2004/0008343 A1 | * | 1/2004 | Pawluczyk et al. | ...... | 356/243.1 |

* cited by examiner

Primary Examiner—F. L. Evans
Assistant Examiner—Kara Geisel
(74) Attorney, Agent, or Firm—Michael A. Glenn; Glenn Patent Group

(57) ABSTRACT

A ceramic reference in conjunction with a spectrometer, a metallized ceramic material, and a method of utilizing a ceramic material as a reference in the ultraviolet, visible, near-infrared, or infrared spectral regions are presented. The preferred embodiments utilize a ceramic reference material to diffusely reflect incident source light toward a detector element for quantification in a reproducible fashion. Alternative embodiments metallize either the incident surface or back surface of to form a surface diffuse reflectance standard. Optional wavelength reference layers or protective layers may be added to the ceramic or to the metallized layer. The reference ceramic is used to provide a measure of optical signal of an analyzer as a function of the analyzers spatial, temporal, and environmental state.

45 Claims, 9 Drawing Sheets

WavCoat4spw

SPECTROSCOPIC SYSTEM AND METHOD USING A CERAMIC OPTICAL REFERENCE

CROSS REFERENCE TO RELATED APPLICATIONS

This application claims priority to U.S. Provisional Patent Application Ser. No. 60/429,777, filed Nov. 26, 2002, and which is incorporated herein in its entirety by this reference thereto.

BACKGROUND OF THE INVENTION

1. Field of the Invention

The invention relates generally to a reference method and apparatus utilized in instruments for optical analysis. In particular, the invention relates to use of optical standards in spectroscopic systems and methods.

2. Discussion of the Prior Art

Spectrometers and References

An analyzer is a spectrometer designed for a specific purpose. Analyzers and a spectrometers have the common characteristics that incident light is delivered to a reference material, observed light is collected off of or from the reference material, and a signal is generated from the collected photons by a detector. The terms analyzer and spectrometer are utilized interchangeably herein.

A standard may be categorized as a calibrated material often with traceable or known parameters such as reflectance at a given wavelength. A standard may alternatively be referred to as a reference. A reference is utilized as a point of comparison and does not have absolutely known or universally accepted parameters. Herein, the terms standard and reference are utilized interchangeably.

Optical spectrometers may be provided in a single beam or in a double beam design. Both single beam and double beam designs commonly utilize a standard material or a reference material. Single beam spectrometers utilize a reference material in substantially the same optical path as the sample at different points in time. Double beam spectrometers utilize a reference material in a light path separate from that of the sample, but at the same point in time. In both a single beam analyzer and a double beam analyzer design, the optical reference may be air, an intensity standard, or a substance optically resembling the sample. It is common, even with the utilization of an air reference or a material with optical properties similar to a sample, to additionally utilize a reference material.

A reference material may be utilized in a number of instrument designs. First, in transmission spectrometers, references are samples utilized in designs where the incident light traverses the material and the light emits from primarily the opposite face of the material. Second, in reflectance spectrometers, mirrored surfaces reflect incident light from a spectrometer source toward a spectrometer detector without notable penetration into the reference standard. A third spectrometer design is a based upon diffuse reflectance where standards scatter incident light. A diffuse reflectance standard may be of two types, surface and body. A surface diffuse reflectance reference scatters incident light at the incident surface, such as a rough mirror. With a body diffuse reflectance reference, the incident light penetrates into the reference where the photons are scattered. Subsequently, some portion of the incident light is diffusely scattered back to the incident surface where it is emitted and coupled to the spectrometer or analyzer detector system.

A signal or spectrum collected utilizing a reference material is often referred to as a reference signal or spectrum, $I_0$. Alternatively, a reference spectrum may be referred to as a single beam spectrum. Optical signals or spectra are utilized in a range of techniques including:

preprocessing;
 processing;
 calibration;
 calibration transfer;
 prediction; and
 outlier detection.

In addition, a reference standard may be utilized in determination of a spectral profile of a spectrometer, to characterize or classify a particular or group of spectrometers, or to remove instrument drift due to environmental factors such as temperature or humidity.

A single beam spectrum may be utilized independently in analyses. However, typically a single beam spectrum is utilized in combination with a sample spectrum. A reference spectrum, $I_0$, may be utilized in calculating transmittance, T, of a sample as in equation 1 where, I is the observed intensity or power of the sample.

$$T = \frac{I}{I_0} \tag{1}$$

A reference spectrum, $I_0$, is also utilized to calculate absorbance as in equation 2 where A is absorbance and I is the observed light collected with the utilization of a sample in the optical train of the analyzer.

$$A = \log_{10} \frac{I_0}{I} = -\log T \tag{2}$$

Often, the selection of a reference material with particular optical characteristics is important for a particular optical design. For example, in a spectrometer it is important to couple the incident light from the source to the detector via a reference material. If the interface is designed such that incident light interacting with the reference is not directed toward the detector, then the design will fail.

Description of Related Technology

A number of commercially available materials are available for use with a spectrometer for generation of a reference signal. Generally, reference materials have common properties including:

non-descript spectral signatures;
 relatively featureless spectral properties;
 homogeneity; and
 stability.

Practical considerations select for reference materials that are affordable, readily produced, easy to utilize, and are cleanable. In addition, a reference material should have resistance to environmental factors such as temperature, light exposure, and humidity.

A common near-IR diffuse reflectance reference material is polytetrafluoroethylene (PTFE). Pressed particles of PTFE are sold commercially under the name of LAB-SPHERE (North Sutton, N.H.).PTFE is a diffuse reflectance standard of approximately 99% reflectance utilized from 250 to 2500 nm. Carbon black may be impregnated into the material to form reference materials ranging from 1 to 99 percent diffuse reflective. While this type of reference is widely utilized, a PTFE body diffuse reflectance reference is expensive, requires a significant thickness, and is not readily cleaned.

G. Christensen and L. Moore, Metallization of a ceramic substrate, U.S. Pat. No. 4,526,859, (Jul. 2, 1985) describe electroplating and vapor deposition of metals onto ceramic substrates is well known in the art of surface coatings. Ceramic substrates have been selectively metallized by depositing metal at only selected portions of a metallization pattern through a customized mask. This technology is utilized for integrated circuit packaging. Coating of the entire surface would not allow creation of an integrated circuit. These materials and this methodology has not been utilized in the nonanalogous art of reference materials.

There exists, however, a need for an affordable reference material with stable optical features that may be compact in size, is resistant to environmental influences, is readily produced, and is easy to utilize.

SUMMARY OF THE INVENTION

The invention provides a ceramic reference material in conjunction with a spectrometer and a metallized ceramic material for use as a reference material in the ultraviolet, visible, near-infrared, or infrared spectral regions. The preferred embodiment utilizes a ceramic reference material to scatter incident source light. Subsequently, the ceramic reference material diffusely reflects the scattered light toward a detector element for quantification in order to measure an optical signal of the spectrometer in a reproducible fashion and to provide a measure of optical throughput of the spectrometer as a function of the spectrometers spatial, temporal, and environmental state. In a second embodiment, the reference ceramic may be metallized to form a surface diffuse reflector. In a third embodiment, wavelength reference layers or protective layers are added to the ceramic or to the metallized layer to create additional reference materials.

DETAILED DESCRIPTION

The preferred embodiment of the invention utilizes a ceramic reference in conjunction with a spectrometer and a method of utilizing a ceramic material as a reference in the ultraviolet, visible, near-infrared, or infrared spectral regions. The optical analyzer includes a source and a detector in an optical train. Incident photons from the source are coupled to the ceramic reference material to obtain a reference signal. Subsequently, the ceramic reference material is utilized to diffusely reflect incident source light toward a detector element to characterize the state of the spectrometer in a reproducible fashion. The reference ceramic is used to provide a measure of the optical signal of an analyzer as a function of the analyzers spatial, temporal, and environmental state.

Spectrometer

Figure 1:
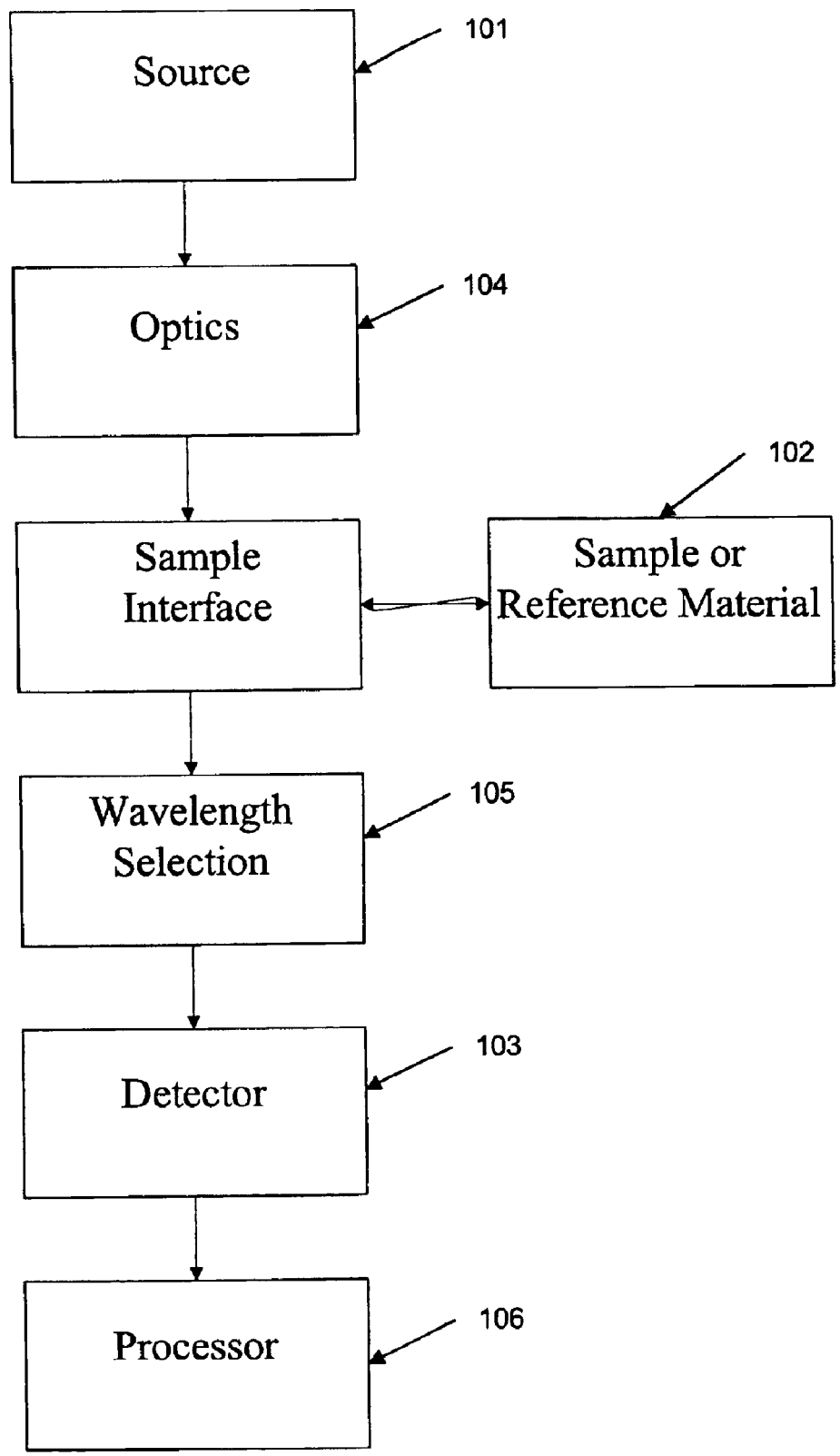
FIG. 1 provides a block diagram of a spectrometer coupled to a reference material.
Figure 2:
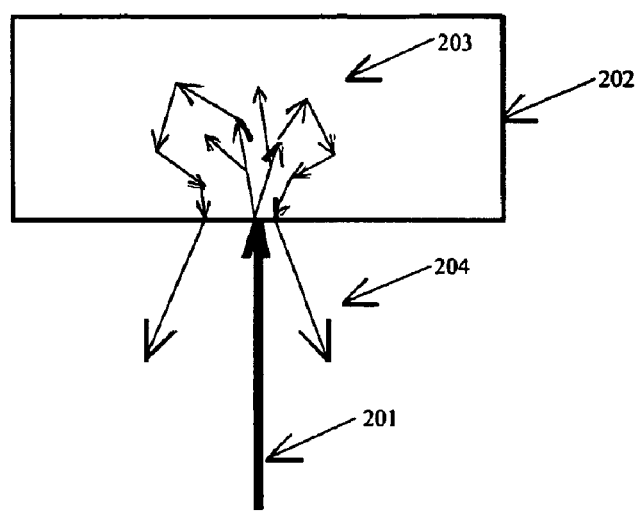
FIG. 2 presents a ceramic material utilized as a body or volume diffuse reflectance standard according to the invention.

A block diagram of a spectrometer is provided in FIG. 1. The spectrometer may analyze one or more wavelengths. Essential elements of the analyzer are a source 101, a sample or reference material 102, and a detector 103. A light source may include:

a blackbody source;

a tungsten-halogen source; and one or more LED's, or one or more laser diodes.

In a single beam analyzer, a ceramic reference material would temporally displace the sample position when a reference signal is collected. The detector may be in the form of one or more single element detectors or one or more arrays or bundles of detectors. In the near-IR, detectors include InGaAs, PbS, PbSe, Si, MCT, detectors or detectors responsive to photonic stimulation in other spectral regions. Light collection optics including fiber optics, lenses, and mirrors are commonly utilized in various configurations within a spectrometer to direct light from the source to the detector by way of a sample or reference material. These optional light collection optics 104 may be utilized anywhere in the optical train in order to enhance standard instrument parameters such as signal and noise. Similarly, an optional wavelength selector 105 such as a grating, Michelson interferometer, or beamsplitter may be incorporated into the optical train of a spectrometer in order to obtain frequency domain information about the sampled light. Typically, a processor 106 is utilized to collect or analyze the detected signal. Utilized spectroscopic techniques include:

Raman;

fluorescence;

ultraviolet (200 to 400 nm);

visible (400 to 700 nm);

near-infrared (700 to 2500 nm or 14,286 to 4000 $cm^{-1}$); and infrared (2500 to 14,285 nm or 4000 to 700 $cm^{-1}$).

The mode of operation may be transmission, reflectance, diffuse reflectance, or transflectance.

Ceramic Reference Material

Ceramics exist in many formulations. The ceramic formulation utilized in the examples provided herein is an aluminum oxide, which is also known as alumina. Other formulations include aluminum nitride, boron nitride, and hundreds of other formulations. In general, a ceramic is prepared as a slurry and is subjected to heat. The heating step also known as firing cures the ceramic and drives off the water to create a ceramic structure. The resulting ceramic structure is porous; the ceramic has physical holes in it. In addition, the cured or calcined ceramic also has optically rough surfaces due to this porosity. The degree of porosity may be controlled by the method of manufacture. In addition, the thermal conductivity of a ceramic may be controlled by the method of manufacture.

A ceramic is an optical diffuse reflectance material that may be utilized as an intensity reference standard. Incident light may be diffusely reflected off of the surface of a ceramic due to its rough structure. Similarly, incident light may penetrate into the internal scattering body of a ceramic due to its porosity. The porosity of the body of the ceramic results in the diffuse reflectance of penetrating photons. In FIG. 1, incident light 201 penetrates through an incident surface 202 into a ceramic 203 where the photons are diffusely scattered 204. A fraction of the incident light is scattered back to the incident surface where it is emitted 205 from the ceramic and directed via optional light collection optics into the analyzer toward a detector. Light penetrating the top surface may transmit through a thin ceramic, allowing for the ceramic to be utilized as a transmission reference sample. Selection of ceramic properties, such as particle size, will affect the required thickness for formation of a transmission or diffuse reflectance reference. As the thickness of the ceramic increases, the amount of transmitted light will decrease to zero and the amount of diffusely reflected light detected will increase to a maximum, allowing for the ceramic to be utilized as a diffuse reflectance reference. Certain ceramics require a total thickness of less than 2.5 mm to maximize the diffusely reflected light emitting from the incident interface surface.

Figure 3:
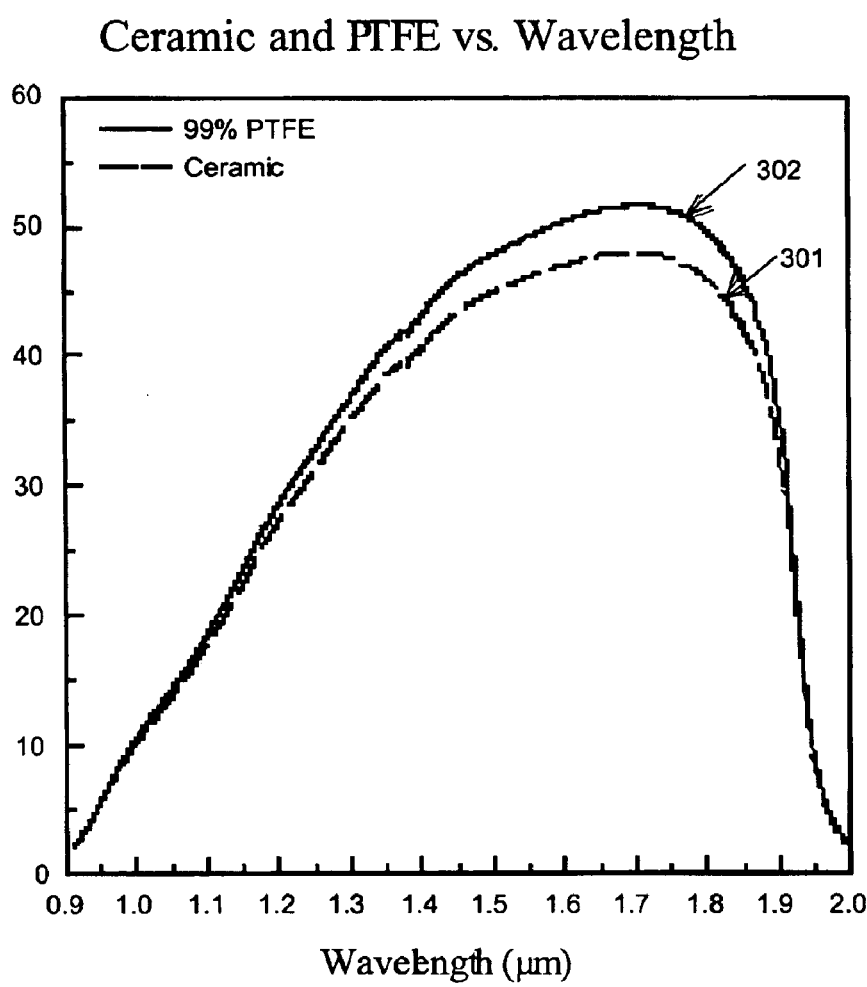
FIG. 3 shows a single beam diffuse reflectance spectrum of a ceramic reference generated with a spectrometer according to the invention.

A spectrum of an uncoated, optically rough, ceramic was obtained in diffuse reflectance mode with a spectrometer. Photons penetrated into the incident surface of a ceramic where they were scattered and partially absorbed. Photons reemerging from the incident side of the ceramic were collected and detected. In FIG. 3, a single beam spectrum from 1100 to 2000 nm quantifying the observed intensity of the ceramic reference 301 as a function of wavelength is provided. The spectrum is overlaid onto a reference spectrum 302 acquired utilizing a polytetrafluoroethylene (PTFE) standard material. Notably, the ceramic single beam spectrum presented diffusely reflects a significant fraction of the incident light as compared with the PTFE standard. Additional tested configurations resulted in single beam spectra where the ceramic reference resulted in larger intensities than the PTFE standard. Conversion of the generated spectra to absorbance reveals that the ceramic reference material has no large absorbance features. The spectrometer utilized in conjunction with the ceramic to produce the reference spectrum provided was configured with an InGaAs detector. The InGaAs response is responsible for the decrease in observed intensity from 1.6 to 0.9 $\mu$m and from 1.7 to 1.95 $\mu$m. Hence, it is the detector and not the ceramic itself that results in major features of the single beam spectrum; the ceramic may be utilized as a reference as noted above from the ultraviolet through the mid-infrared spectral regions.

In the present embodiment, a ceramic was utilized in conjunction with a spectrometer to provide a reproducible quantification of spectral signal characterizing the spatial and temporal characteristics of the spectrometer. The tested aluminum oxide ceramic is to be insensitive to environmental changes, such as temperature and humidity, making it an excellent choice as a reference material. In addition, ceramics may be manufactured in a cost effective manner.

Metallized Ceramic

An alternative equally preferred embodiment of the invention utilizes a metallized ceramic reference material in conjunction with a spectrometer or optical analyzer. The optical analyzer designs that may be utilized in with the metallized ceramic are well known to those skilled in the art, may be as described in the background section, and may be as in the preferred embodiment described above.

Figure 4:
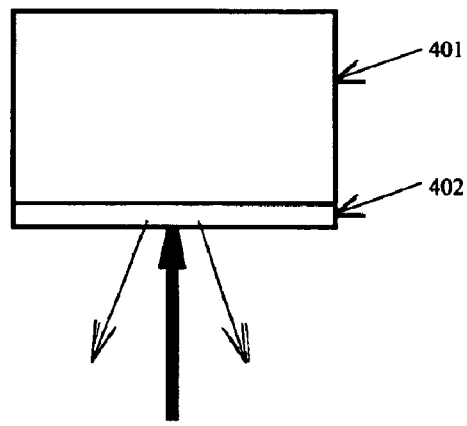
FIG. 4 shows a ceramic material metallized on an incident surface according to the invention.

In this alternative embodiment of the invention, at least the incident surface of a ceramic is metallized, where the metallized layer replicates the rough surface of the ceramic composite to act as a scattering surface to the incident photons, FIG. 4. A ceramic material 401 may be metallized on at least the incident surface with a first layer 402. The surface of the ceramic interfacing with the incident light is optically rough or scattering. The applied metallized coating may be any reflective material such as gold, silver, aluminum, platinum, chromium, lead, copper, or the like. Alloys may also be utilized. Vapor deposition, electroplating, silk screening, metal filled epoxy, and other methods commonly known to those skilled in the art may be utilized to deposit the metallized layer on either the incident surface. The metallized surface substantially replicates the rough ceramic surface.

Figure 5:
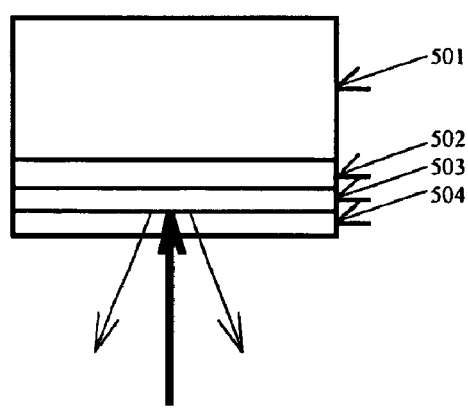
FIG. 5 presents a ceramic material sequentially coated with two metallized layers, and a protective layer to be utilized as an incident surface diffuse reflectance intensity standard according to the invention.

Some materials do not readily adhere to ceramic. For example, gold may flake off of a ceramic. This problem may be alleviated, FIG. 5, with the utilization of an intermediate metallized layer 501 deposited onto a ceramic 502. While this intermediate or first layer may be any material such as the metals listed above, a preferred first contact layer with the ceramic is chromium. Chromium is utilized due to its adhesive characteristics to help bond a second metallized layer, such as gold, to the ceramic. In general, a second metallized 503 layer may then be deposited to the first layer. If necessary, additional metallized layers may be sequentially applied. Each layer may be any of the metals or alloys listed above and techniques for depositing these layers are as described above.

A final protective layer 504 may be applied to the outermost metallized layer of any of the above embodiments. This protective layer need not be metallic, but may be a coating of aluminum oxide, sapphire, or optically clear epoxys. The spectral characteristics of the optional protective layer should be controlled. Absorbance features of the protective layer should not absorb in the spectral region of interest or should be small in magnitude at the thickness of the protective layer utilized. For example, when building a near-IR standard to be utilized from 700 to 2500 nm, a wax coating would be inappropriate due to the large carbon-hydrogen absorbance bands that would be present in the near-IR region. This is particularly be true in the second overtone region from 1100 to 1400 nm, the first overtone region from 1500 to 1900 nm, and in the combination band region from 2100 to 2400 nm. In addition, because the front side or incident side of the ceramic that is acting as the scatterer, the protective coating layer needs to fundamentally maintain the surface features of the ceramic. Each of the metallized layers on the incident surface of the ceramic should maintain the fundamental roughness of the surface of the ceramic in order to provide the material scattering properties.

Coating techniques, such as vapor deposition, don't completely replicate the surface of the ceramic. This is acceptable as long as the resulting surface acts as a scatterer.

Figure 6:
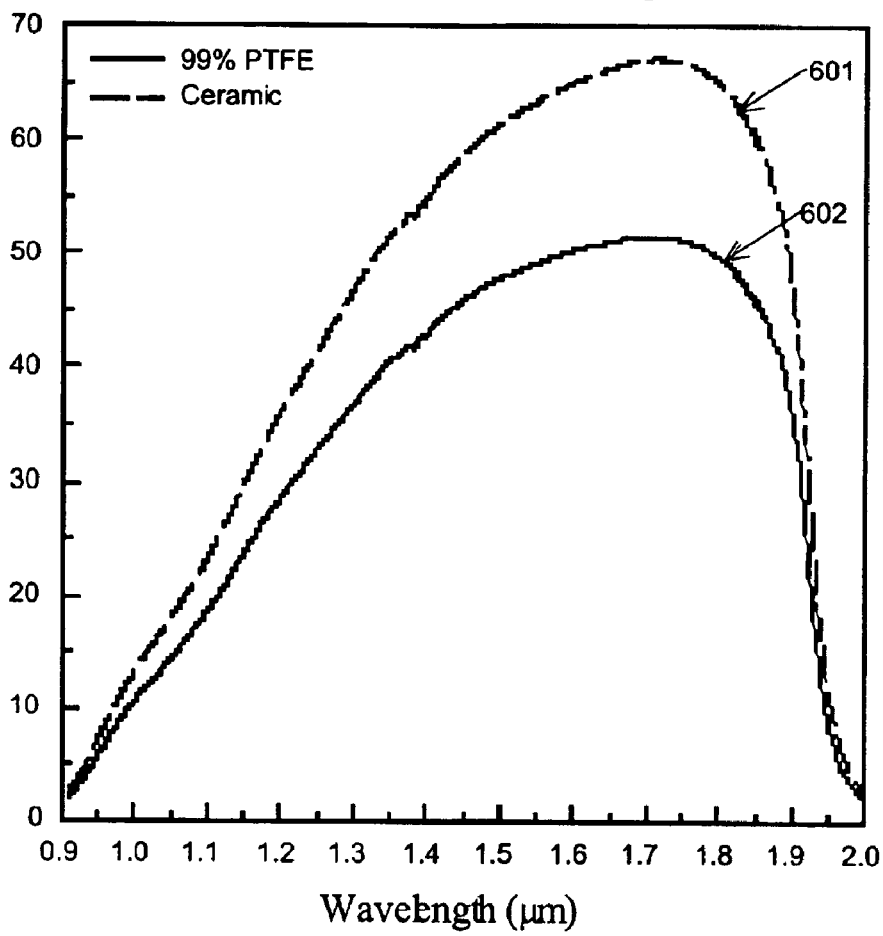
FIG. 6 shows a single beam diffuse reflectance spectrum of a metallized ceramic reference and a PTFE reference generated with a spectrometer according to the invention.

A reference spectrum obtained utilizing a ceramic metallized with a single layer on the incident surface in conjunction with a spectrometer configured in diffuse reflectance mode is provided, FIG. 6. A gold-coated, optically rough, ceramic was scanned in diffuse reflectance mode. Incident photons diffusely scatter off of the outermost rough metallic layer. Scattered photons were collected and subsequentially detected. A single beam spectrum from 1100 to 2000 nm showing the observed intensity of the gold coated ceramic 601 as a function of wavelength is overlaid with a single beam spectrum of a 99% PTFE standard 602 generated with the same spectrometer configuration. Those skilled in the art will recognize that the slopes of the single beam spectra are due to the particular instrument configuration utilized. In this case the metallized ceramic returns more diffusely reflected light than the PTFE reference, which is a function of the optical geometry of the spectrometer. As in FIG. 3, the resulting single beam metallized ceramic spectrum demonstrates a high reflectance and an absorbance free signal. These characteristics demonstrate that a ceramic metallized on the incident surface performs to acceptable levels as a reference material.

In a further alternate embodiment of the invention, incident light from a spectrometer strikes the front side or incident side of the ceramic, penetrates into a ceramic, and is scattered. The opposite side of the ceramic is herein referred to as the back surface. The back surface of the ceramic is metallized utilizing standard coating techniques described below. Coating the backside of the ceramic creates a volume diffuse reflectance material. If the ceramic is thin relative to the scattering some photons scatter/transmit through the ceramic where they are reflected off of the metallized layer that has been coated onto the backside of the ceramic to act as a mirror or backreflector to the photons that penetrate through the ceramic. Photons do not penetrate through the metallized back layer. A portion of the reflected photons retransmit through the ceramic to the incident surface where they are emitted and detected. This configuration allows for a thin ceramic to be utilized as a diffuse scattering element. If no metallized or reflective coating is placed on the back of a ceramic, the ceramic must be thick enough to return an acceptable signal via scattering to the incident or front surface of the ceramic. Therefore, a back metallized coating increases the observed intensity of an optically thin ceramic reference. For example, the ceramic may be less than 1 mm thick. There are several cases in which it is desirable to utilize a thinner ceramic. For example, the cost of the ceramic increases with the total volume utilized, so a thinner and therefore less expensive reference may be desired. Additional examples include situations in which a thicker ceramic is sterically prohibited or a lighter reference is desired.

The applied metallized coating may be any reflective material such as gold, silver, aluminum, platinum, chromium, lead, copper. Alloys may also be utilized. Vapor deposition, electroplating, and other methods commonly known to those skilled in the art are suitable for depositing the metallized layer on either the incident or back surface. It is recognized that some materials do not bond readily directly to ceramics. More than one metallized layer may be deposited. The first layer may be utilized due to its adhesive characteristics. A second metallized layer may then be deposited as above onto the first layer. For example, the first layer in contact with the backside of the ceramic may be chromium. A second layer such as gold may be deposited onto the chromium layer. In this example, chromium is utilized due to its adhesive characteristics to help bond the gold layer to the ceramic. If necessary, additional metallized layers could be sequentially applied. The metallized layers reflect the light that traverses the sample in a manner similar to a mirror placed behind the ceramic. However, the metallized layer essentially replicates the rough surface of the ceramic so that the reflected light is diffuse.

An optional final protective layer may be applied. The protective layer has benefits including allowing the reference surface to be cleaned and protecting the outer layer from chipping or flaking. Examples of protective layers include aluminum oxide or sapphire.

The present embodiment has the further advantage that the metallized layer or layers may be deposited in a manner that does not need to replicate the surface roughness of the ceramic. For example, a mirrored or smooth back surface is acceptable. This allows faster or cheaper methods such as dip coating or equivalents to be utilized to coat the back surface of the ceramic in addition to the application methods described above. This is acceptable as it is the ceramic that is acting as the diffuse reflector.

The optional protective layer coating the outermost metal surface on the back of the ceramic may be diverse in its qualities. For example, if a near-IR standard is desired, the protective coating layer on this standard may absorb broadly and/or sharply in the near-infrared region as the photons will not penetrate the metallized layer to sample the protective coating. Hence the protective coating need only protect the inner metallized layer(s). Many types of protective layers are employed such as paints, glasses, plastics, waxes, sapphire, aluminum oxide, and the like. It is the function of the protective layer that is important, which is to prevent the metallized layer from chipping, peeling, or otherwise disattaching from the ceramic.

In a still further alternative embodiment, a wavelength reference coating is applied to a ceramic or to one or more metal layers applied to the ceramic wherein the absorption characteristics of the coating behave as a wavelength standard. A wavelength standard has the characteristic of having known or reproducible absorbance bands in a given environmental state. These known absorbance bands may behave in a known fashion under varying conditions such as varying temperature or humidity.

Figure 7:
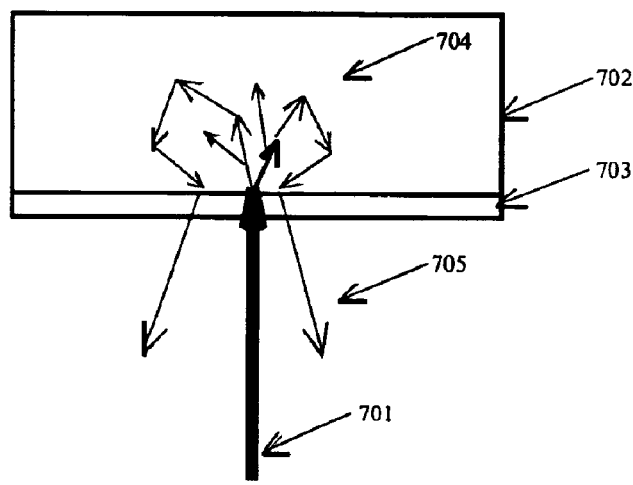
FIG. 7 presents a ceramic coated with a wavelength reference material according to the invention.

The present embodiment is shown in FIG. 7. Incident light 701 is penetrates through a wavelength reference layer 702 coated onto the incident surface of a ceramic material 703. Photons further penetrating into the ceramic where they are diffusely scattered 704 as described above. A portion of this light re-penetrates through the wavelength reference standard and are detected 705. According to Beer's Law, the thickness of the reference layer will have a direct impact on the magnitude of the wavelength standard absorbance bands observed. An optional protective layer may be applied to the wavelength reference layer. The protective layer may be sapphire, aluminum oxide, clear epoxy, and the like.

Figure 8:
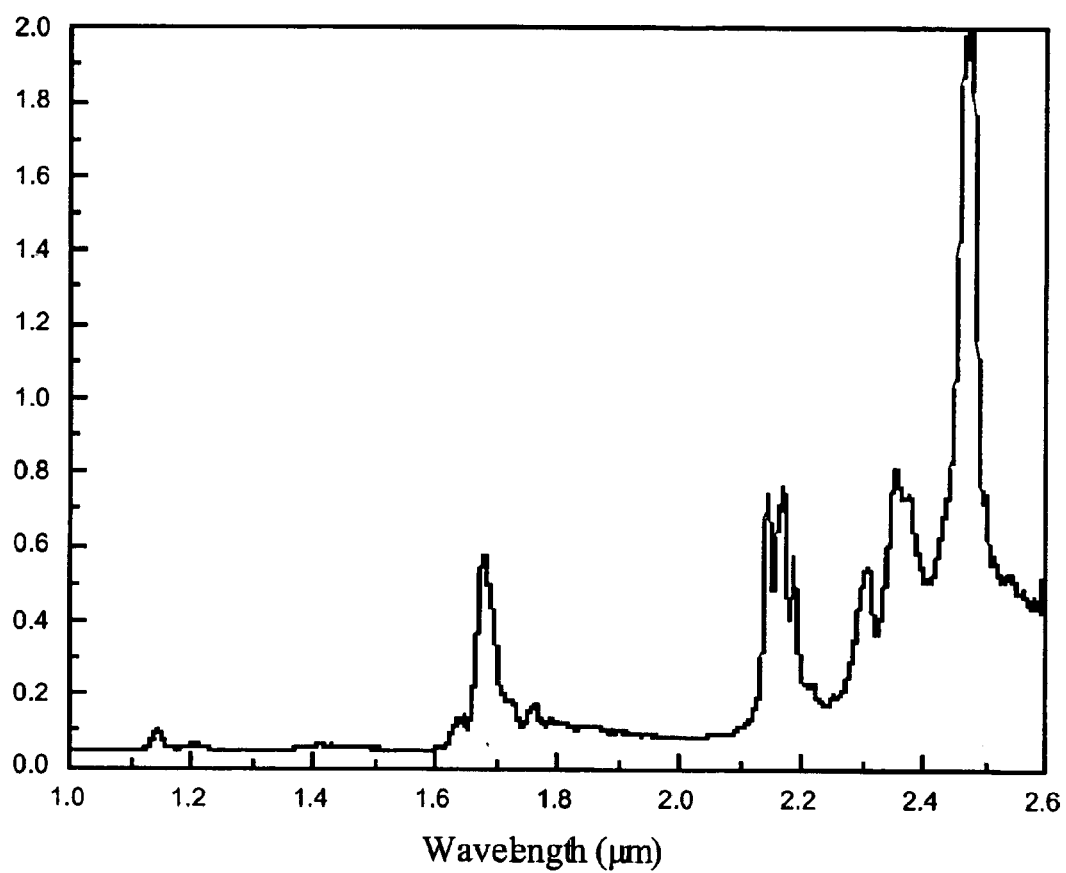
FIG. 8 presents a polystyrene absorbance spectrum.
Figure 9:
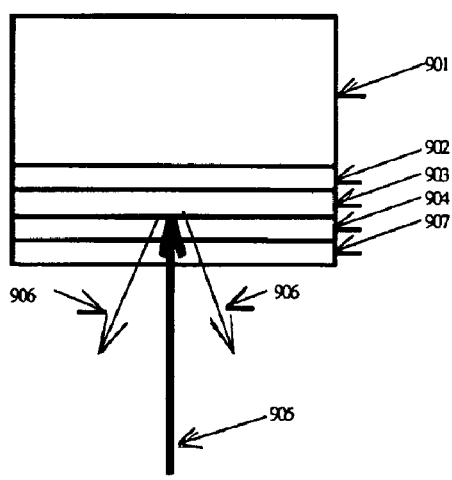
FIG. 9 shows a ceramic coated sequentially with two metallized layers, a wavelength reference layer, and a protective layer according to the invention according to the invention.

The wavelength reference layer is composed of a material with desirable spectral features, such as features that are broad and stable in the environmental condition utilized. Some common wavelength reference materials in the near-IR include: polystyrene, polyethylene, polypropylene, epoxy, plastic, erbium oxide, holmium oxide, dysprosium oxide, and the like. FIG. 8 shows key absorbance bands used for wavelength calibration in an absorbance spectrum of polystyrene.

Notably, more than one wavelength reference layer may be applied. For example, one layer may be holmium oxide, a second layer may be dysprosium oxide, and a third layer may be erbium oxide. Each layer would add particular absorbance features useful in wavelength calibration, determination, quality assurance, or quality control of a spectrometer.

In yet another embodiment of the invention, a ceramic 901 may be coated with a first 902, a second 903, and, optionally, a third metallized layer on the incident side of a ceramic. As in previously described embodiments, the metallized layers can be composed of any reflective material such as gold, silver, aluminum, platinum, chromium, lead, copper, and the like. A wavelength reference layer(s) 904 as described above is applied to the outermost metallized surface the coated ceramic. This configuration allows the incident light 905 to traverse the wavelength reference layer and to be diffusely scattered by the outermost metallized layer before reemitting 906 from the reference conglomerate toward the detector. An optional protective coating 907 may be applied to the wavelength reference layer.

The resulting single beam or calculated absorbance spectra can then be utilized as reference spectra for wavelength determination, wavelength standardization, wavelength adjustment, or calibration transfer.

Common Embodiment Elements

Numerous embodiments have been described above. One will note that many permutations and combinations of the elements of the above embodiments are possible and that many similarities exist between the embodiments. A number of examples follow.

Angle of Incidence

In each embodiment, the angle of the incident light to the surface is preferably normal. However, the angle of the incident variation onto the standard may be varied. This may be done, for example, to minimize or eliminate spectral reflectance.

Layer Thickness

The thickness of the ceramic substrate may vary, and/or the thickness of each metallized layer may vary. For example, the period of vapor deposition of a given metallic layer may be varied to control the thickness of that given layer. Similarly, the thickness of a wavelength reference layer may be varied. One benefit of varying the wavelength standard layer thickness is to control the magnitude of the absorbance features utilized for x-axis determination, calibration, quality assurance, quality control, or calibration transfer. Similarly, the thickness of a protective layer may vary.

Coatings

Anti-reflection (A/R) coatings or index of refraction coatings may be utilized on or between layers such as the protective layer or wavelength standard layer. One advantage of an A/R coating is to increase spectral throughput.

Shape

A ceramic reference material may be made in the shape of a standard such as a circular disc or a rectangular block. The actual shape is dependent upon the reference to spectrometer interface. Typically, the standard is mounted into a holder and have at least one flat surface upon which the incident light from the spectrometer strikes. The flat surface of the ceramic is, in fact, optically rough and cause the incident light to scatter. The shape and surface area of the interface side of the ceramic is dependent upon the geometry of the spectrometer. For example, for light emitted from a single fiber optic or from a fiber optic bundle, a ceramic disc is utilized where the incident light strikes a circular surface. The diameter of the disc is be dependent upon at least the numerical aperture of the fiber material and distance to the ceramic material. A larger distance between the fiber tip and the reference position requires a larger ceramic due to the conical expansion of the incident light with distance. The speed of the optics dictates the diameter of the ceramic. Preferably, the ceramic exceeds the optical spot size by at least 1 mm in all directions. Similarly, a rectangular incident surface of a ceramic is utilized for incident light emerging from a rectangular slit. Again the size is dependent upon the particular interface to the spectrometer.

Distance

The distance of the ceramic from the spectrometer interface impacts returned intensity. For example, as the distance from a light collection optic such as a fiber optic is increased, the collected light returning from the ceramic decreases and the apparent intensity decreases. Thus variation in the distance between the radiation source and the ceramic reference may be utilized as an intensity or gain control. That is, the number of collected photons may be modified as a function of distance between the source and/or collection optics and the ceramic reference standard.

Applications

The use of a ceramic or metallized ceramic as a standard or as a reference with any photometric device that utilizes a standard or reference material is entirely consistent with the spirit and scope of the invention. The field of noninvasive spectroscopy provides a particular example of use of a ceramic reference with an analyzer. One embodiment is the near-IR noninvasive determination of glucose. Analyzers have been previously described in S. Malin, G. Khalil, Method and apparatus for multi-spectral analysis of organic blood analytes in noninvasive infrared spectroscopy, U.S. Pat. No. 6,040,578, (Mar. 21, 2000) and G. Acosta, J. Henderson, N. Abul-Haj, T. Ruchti, T. Blank, K. Hazen, and D. Grubisic, Compact apparatus noninvasive measurement of glucose through near-infrared spectroscopy, PCT/US03/07065, (Mar. 7, 2003), which are herein incorporated by reference and are commonly owned with the present application.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. A method of generating a reference signal, comprising steps of:
   providing a spectrometer having a source that emits incident photons;
   providing an optically rough ceramic element having an incident surface and an internal scattering body;
   directing at least a portion of said incident photons toward said incident surface;
   scattering said at least said portion of said incident photons by said ceramic; and
   detecting at least a portion of said scattered photons, wherein said reference signal is generated.

2. The method of claim 1, wherein said scattered photons result from physical interaction with at least one of:
   said incident surface; and
   said internal scattering body.

3. The method of claim 2, wherein said incident surface of said ceramic diffusely reflects said incident photons.

4. The method of claim 1, wherein said spectrometer comprises either a single beam analyzer or a dual beam analyzer.

5. The method of claim 1, further comprising a step of:
   operating said spectrometer in diffuse reflectance mode or in transflectance mode.

6. The method of claim 1, wherein said spectrometer further comprises at least one of:
   a coupling optic;
   a sample interface optic, separated by a distance from said ceramic; and
   a wavelength separation device.

7. The method of claim 6, wherein said coupling optic is positioned after said ceramic element.

8. The method of claim 6, further comprising:
   a step of varying said distance between said ceramic and said interface optic in order to increase or decrease said signal.

9. The method of claim 6, wherein said wavelength selection device comprises any of:
a prism;
a grating; and
a Michelson interferometer.

10. The method of claim 1, wherein said reference signal comprises a reference spectrum.

11. The method of claim 1, wherein said spectrometer comprises a noninvasive glucose analyzer.

12. The method of claim 2, further comprising a step of:
coating said incident surface of said ceramic with a first layer contacting and completely covering said incident surface of said ceramic.

13. The method of claim 12, wherein said first layer comprises at least one of:
a wavelength reference layer; and
a protective coating.

14. The method of claim 13, wherein said wavelength reference layer comprises at least one of:
polystyrene;
polyethylene;
polypropylene;
epoxy;
plastic;
erbium oxide;
holmium oxide; end
dysprosium oxide.

15. The method of claim 13, wherein said incident photons and said scattered photons are at least partially absorbed by said wavelength reference layer.

16. The method of claim 15, further comprising a step of:
utilizing said signal to generate at least one of a transmittance value and an absorbance value.

17. The method of claim 13, wherein said protective coating comprises any of:
sapphire;
aluminum oxide;
an optically clear epoxy; and
plastic.

18. The method of claim 12, wherein said first layer comprises:
a first metallized coating,
wherein said first metallized coating scatters said at least a portion of said incident light, preventing said at least a portion of said incident light from penetrating into said internal scattering body of said ceramic.

19. The method of claim 18, wherein said first metallized coating comprises at least one of:
gold;
silver;
aluminum;
platinum;
chromium;
lead; and
copper.

20. The method of claim 18, further comprising a step of:
coating said first layer with a second layer in continual contact with and coated over entire said first layer.

21. The method of claim 20, wherein said second layer comprises at least one of:
a standard wavelength material; and
a protective coating.

22. The method of claim 21, wherein said standard wavelength material comprises any of:
polystyrene;
polyethylene;
polypropylene;
epoxy;
plastic;
dysprosium oxide;
erbium oxide; and
holmium oxide.

23. The method of claim 21, further comprising a step of:
utilizing said signal to generate at least one of a transmittance value and an absorbance value.

24. The method of claim 21, wherein said protective coating comprises any of:
sapphire;
aluminum oxide;
an optically clear epoxy; and
plastic.

25. The method of claim 20, wherein said second layer comprises:
a second metallized coating.

26. The method of claim 25, wherein said second metallized coating is any of:
gold;
silver;
aluminum;
platinum;
chromium;
lead; and
copper.

27. The method of claim 25, further comprising a step of:
applying a third layer in contact with and completely covering said second layer, wherein said third layer is at least one of:
a standard wavelength material; and
a protective coating.

28. The method of claim 27, wherein said standard wavelength material comprises any of:
polystyrene;
polyethylene;
polypropylene;
epoxy;
plastic;
dysprosium oxide;
erbium oxide; and
holmium oxide.

29. The method of claim 28, further comprising a step of:
utilizing said signal to generate either a transmittance value or an absorbance value.

30. The method of claim 27, wherein said protective coating comprises any of:
sapphire;
aluminum oxide;
an optically clear epoxy; and
plastic.

31. An apparatus for generating a reference signal, comprising:

a ceramic having an incident surface and a back surface;

a first layer in continual contact with end coated over at least one of either said incident surface or said back surface, wherein said first layer comprises at least one of:

a first standard wavelength material;

a first protective coating; and a first metallized coating;

wherein at least one of said incident surface and said back surface is optically rough.

32. The apparatus of claim 31, wherein said incident surface is flat.

33. The apparatus of claim 31, wherein said first standard wavelength material comprises at least one of:

polystyrene;

polyethylene;

polypropylene;

epoxy;

plastic;

dysprosium oxide;

erbium oxide; and holmium oxide.

34. The apparatus of claim 31, wherein said first protective coating comprises any of:

sapphire;

aluminum oxide; and plastic.

35. The apparatus of claim 31, wherein said first metallized coating comprises at least one of:

gold;

silver;

aluminum;

platinum;

chromium;

lead; and copper.

36. The apparatus of claim 31, further comprising:.

a second layer in continual contact with and coated over said first layer.

37. The apparatus of claim 36, wherein said second layer comprises at least one of:

a secondary wavelength material;

a secondary protective coating; and a secondary metallized coating.

38. The apparatus of claim 37, wherein said secondary standard wavelength material comprises at least one of:

polystyrene;

polyethylene;

polypropylene;

epoxy;

plastic;

dysprosium oxide;

erbium oxide; and holmium oxide.

39. The apparatus of claim 37, wherein said secondary protective coating comprises any of:

sapphire;

aluminum oxide; and plastic.

40. The apparatus of claim 37, wherein said secondary metallized coating comprises any of:

gold;

silver;

aluminum;

platinum;

chromium;

lead; and copper.

41. The apparatus of claim 36, further comprising:

a third layer in continual contact with and coated over entire said second layer.

42. The apparatus of claim 41, wherein said second layer comprises:

an outer protective coating.

43. The apparatus of claim 42, wherein said outer protective coating comprises any of:

sapphire;

aluminum oxide; and plastic.

44. A method of generating a reference signal, comprising steps of:

providing a spectrometer having a source that emits incident photons;

providing a ceramic material having an incident surface and a metallized back surface;

directing said incident photons through said incident surface, wherein at least a portion of said incident photons traverse said ceramic material and are diffusely reflected by said metallized back surface and subsequently emitted from said incident surface; and detecting said emitted photons, wherein a reference signal is generated.

45. The method of claim 44, wherein said metallized back surface of said ceramic is optically rough, such that light hitting said metallized back surface is either reflected or scattered.

* * * * *